(12) United States Patent
Moore (10) Patent No.: US 9,568,296 B2
(45) Date of Patent: Feb. 14, 2017

(54) BREAST MEASURING DEVICE FOR DETERMINING BRA SIZE

(71) Applicant: Ing. Gerhard Fildan GesmbH, Ebenfurth (AT)

(72) Inventor: Wendy Moore, Cork (IE)

(73) Assignee: Ing. Gerhard Fildan GesmbH, Ebenfurth (AT)

( * ) Notice: Subject to any disclaimer, the term of this patent is extended or adjusted under 35 U.S.C. 154(b) by 0 days.

(21) Appl. No.: 14/388,562

(22) PCT Filed: Mar. 27, 2013

(86) PCT No.: PCT/EP2013/056632
§ 371 (c)(1),
(2) Date: Sep. 26, 2014

(87) PCT Pub. No.: WO2013/144264
PCT Pub. Date: Oct. 3, 2013

(65) Prior Publication Data
US 2015/0089824 A1    Apr. 2, 2015

(30) Foreign Application Priority Data

Mar. 27, 2012  (GB) .................................. 1205364.1

(51) Int. Cl.
*G01B 3/10* (2006.01)
*A41H 1/02* (2006.01)
(Continued)

(52) U.S. Cl.
CPC ............... *G01B 3/1005* (2013.01); *A41H 1/02* (2013.01); *A61B 5/1072* (2013.01);
(Continued)

(58) Field of Classification Search
CPC .............. A41H 1/02; A41H 3/00; A41H 3/04; A41H 21/00; A41H 5/01; A41H 5/02
(Continued)

(56) References Cited

U.S. PATENT DOCUMENTS 1,935,998 A * 11/1933 Strading .................. A41H 1/02
                                                        33/15
2,428,980 A   10/1947 McCann
(Continued)

OTHER PUBLICATIONS

International Search Report issued in PCT/EP2013/056632 on Jun. 21, 2013 by the European Patent Office.

*Primary Examiner* — Yaritza Guadalupe-McCall
(74) *Attorney, Agent, or Firm* — Brian J. Colandreo; Michael T. Abramson; Holland & Knight LLP (57) ABSTRACT

This invention relates to a breast measuring device (1) for determining bra size. The breast measuring device comprises a band size measuring tape (3, 43) and a cup size measuring tape (5, 7) mounted on and extending substantially perpendicular to the band size measuring tape. The band size measuring tape comprises a flexible tape having indicia (19) printed thereon representative of band sizes and the cup size measuring tape comprises a flexible tape having indicia (23) printed thereon indicative of cup sizes. The breast measuring device (1) has a buckle (53) mounted on one end of the band size measuring tape through which the other end of the band size measuring tape (3, 43) may be led and there is provided means (17, 29, 57) to releasably secure the band size measuring tape in a looped configuration. When the device is secured in a looped configuration, the cup size measuring tape (5, 7) can be used to measure the cup size and both the band size and the cup size will be visible simultaneously.

14 Claims, 9 Drawing Sheets

(51) Int. Cl.
  *A61B 5/107* (2006.01)
  *A61B 5/00* (2006.01)
  *A41C 5/00* (2006.01)
(52) U.S. Cl.
  CPC .............. *A61B 5/4312* (2013.01); *A41C 5/00* (2013.01); *G01B 2003/1007* (2013.01)
(58) Field of Classification Search
  USPC .......................................................... 33/512
  See application file for complete search history.

(56) References Cited

U.S. PATENT DOCUMENTS

| | | | | |
|---|---|---|---|---|
| 2,559,501 A * | 7/1951 | Graf | .................... | A41H 1/02 33/2 R |
| 2,575,343 A * | 11/1951 | Heiman | .................. | A41H 1/02 33/2 R |
| 2,946,125 A * | 7/1960 | Gittelson | ................ | A41H 1/02 33/2 R |
| 4,920,659 A | 5/1990 | Becher | | |
| 5,414,943 A * | 5/1995 | Vogt | ........................ | A61B 5/107 33/512 |
| 5,485,855 A * | 1/1996 | Shiraiwa | ................. | A41H 1/02 33/511 |
| 5,965,809 A * | 10/1999 | Pechter | ................... | A41H 1/02 73/149 |
| 6,272,761 B1 * | 8/2001 | Pechter | ................... | G01B 3/02 33/17 R |
| 6,276,069 B1 * | 8/2001 | Chadwick | ............... | A41H 1/02 33/512 |
| 6,415,525 B1 * | 7/2002 | Watkins | ................... | A41H 1/02 33/512 |
| 6,467,180 B1 * | 10/2002 | Chan | ....................... | A41H 1/02 33/17 R |
| 6,640,460 B1 * | 11/2003 | Nabarro | .................. | A41O 5/00 33/512 |
| 8,397,391 B2 * | 3/2013 | Ohly | ....................... | A41C 3/00 33/17 R |
| 8,549,763 B2 * | 10/2013 | Krawchuk | .............. | A41B 9/00 33/17 R |
| 2010/0242291 A1 * | 9/2010 | Ohly | ....................... | A41H 1/02 33/17 R |
| 2013/0074353 A1 * | 3/2013 | Petter | ..................... | A41H 1/02 33/512 |
| 2015/0089824 A1 * | 4/2015 | Moore | .................... | A41H 1/02 33/512 |
| 2015/0342266 A1 * | 12/2015 | Cooper | ................. | A41B 11/00 33/2 R |

* cited by examiner

BREAST MEASURING DEVICE FOR DETERMINING BRA SIZE

RELATED APPLICATIONS

The subject application is a U.S. National Stage Application of International Application No. PCT/EP2013/056632, filed on Mar. 27, 2013, which claims the priority of Great Britain Patent Application No.:1205364.1, filed on Mar. 27, 2012. The entire contents of which are herein incorporated by reference in its entirety.

TECHNICAL FIELD

This invention relates to a breast measuring device for determining the correct size of brassiere (hereinafter referred to simply as bra).

BACKGROUND ART

It is a well-documented fact that a high percentage of women worldwide wear the wrong bra size due to poor measurement. It is very important for women and girls to wear the correct size of bra. Failure to wear the correct size of bra can result in many problems including, but not limited to, health issues for the wearer. For example, if the bra is too small for the wearer it will have a tendency to distort the wearer's posture, causing the wearer to lean forward. This distorted posture puts pressure on the spine and internal organs of the wearer and over time can lead to a loss of muscle definition. In addition to health problems, an ill-fitting bra can be aesthetically displeasing as it can cause the breasts to look larger than they actually are. Poor posture and/or poor aesthetics can, over time, lead to a confidence issue for the wearer.

A woman's breast size will change over time and therefore it is important to periodically measure the breasts to ensure that the bra size being worn is correct. In order to ascertain the correct bra size, there are two essential measurements that must be obtained, band size and cup size. The band size is a measurement corresponding to the circumference of the wearer's torso at a level just below the breast. For example, in the UK and US, typically, the band size is four or five inches more than the circumference of the torso at this point. The band size is usually identified by a two digit number. Other regions often will have different measurement starting points, different measurement units and different increments. The cup size is a measure corresponding to the volume of the breast and is usually identified by one or more letters. For example, 32B and 34C are examples of two different bra sizes (according to the UK measurement system) with different band measurements (32 and 34 respectively) and different cup sizes (B and C respectively).

Unfortunately, it is all too common for women and girls to wear an ill-fitting bra. There are many reasons why this is the case. One reason that is often postulated is that many women are uncomfortable being measured for a bra and are therefore reluctant to be measured. Another reason is that the measurement, particularly if carried out by the woman herself, is performed incorrectly.

There are several tools available for determining the correct bra size for a woman. For example, WO02/39052 in the name of Morplan Limited, EP1,178,280 in the name of Lunaire, Inc., U.S. Pat. No. 6,272,761 in the name of Pechter, U.S. Pat. No. 2,946,125 in the name of Gittelson, U.S. Pat. No. 5,485,855 in the name of Shiraiwa et al and GB870,050 in the name of Inventex all describe measuring devices for determining the correct bra size. There are however problems with the known measuring devices. For example, some of the known measuring devices require the user to memorise measurements, perform mental arithmetic or refer to look-up tables which can be confusing and can lead to errors in measurement. Some of the known measuring devices are relatively complex or cumbersome to use and require the assistance of a third party which can cause discomfort and embarrassment.

It is an object of the present invention to provide a measuring device for determining bra size that overcomes at least some of the problems with the known devices. It is a further object of the present invention to provide a measuring device for determining bra size that is simple and intuitive to use, that is accurate and that can be operated without the assistance of a third party if desired. It is a further object of the present invention to provide a breast measuring device that offers an alternative choice to the consumer.

SUMMARY OF INVENTION

According to the invention there is provided a breast measuring device for determining bra size comprising a band size measuring tape and a cup size measuring tape mounted on and extending substantially perpendicular to the band size measuring tape, the band size measuring tape comprising a flexible tape having indicia printed on one side thereof indicative of a plurality of band sizes, the cup size measuring tape comprising a flexible tape capable of following the contour of a breast and having indicia printed on one side thereof indicative of a plurality of cup sizes, and in which there is provided a first buckle mounted on one end of the band size measuring tape through which the other end of the band size measuring tape may be led thereby forming a loop with the band size measuring tape to surround the torso of a person being measured and means to releasably secure the band size measuring tape in the looped configuration.

By having such a measuring device, it will be possible to determine the bra size in a simple and efficient manner. Furthermore, it will be possible for the woman to measure herself accurately and with ease without the assistance of a third party if she so desires. This is due in part to the fact that the band size measuring tape can be secured in position around the torso with ease, the measurement of the band size can be clearly identified while in this position by viewing where the band size measuring tape passes through the first buckle, and the cup size measurement can be ascertained simultaneously. In this way, it will not be necessary for the woman to memorise measurements, perform mental arithmetic or refer to lookup tables.

In one embodiment of the invention there is provided a measuring device in which there is provided an elasticated portion to permit limited expansion and contraction of the circumference of the loop in the band size measuring tape when secured in a looped configuration. This is seen as a particularly advantageous aspect of the present invention. By providing an elasticated portion, there is less likely to be an error of measurement of the band size caused by the measurement being taken erroneously at maximum expansion of the chest cavity while the woman is inhaling. The elasticated portion will allow the chest circumference of the loop in the band size measuring tape to expand and contract by a limited amount as the woman breathes thereby allowing the correct band size measurement to be taken.

In one embodiment of the invention there is provided a measuring device in which the elasticated portion has attached thereto the means to releasably secure the band size measuring tape in the looped configuration. This is seen as a particularly useful way of implementing the elasticated portion as the band tape itself will not have to be elasticated and therefore there will not be a tendency for the user to inadvertently stretch the band size measuring tape and take an incorrect band size reading.

In one embodiment of the invention there is provided a measuring device in which the elasticated portion is mounted on the band size measuring tape intermediate the ends of the band size measuring tape and adjacent to one end thereof. Importantly, the elasticated portion will be located in a position along the band size measuring tape so that it engages the other end of the band size measuring tape in a location after the other end of the band size measuring tape has passed through the first buckle. This will prevent a distorted band size measurement being taken.

In one embodiment of the invention there is provided a measuring device in which the means to releasably secure the band size measuring tape in the looped configuration comprises a second buckle mounted on the elasticated portion and through which the end of the band size measuring tape led through the first buckle may also be led and secured in position. This is seen as a simple and secure way of securing the band size measuring tape in position.

In one embodiment of the invention there is provided a measuring device in which the means to releasably secure the band size measuring tape in the looped configuration comprises a pair of complementary locking members and in which the elasticated portion has one part of the pair of complementary locking members mounted thereon for engagement of the other part of the pair of complementary locking members which in turn is mounted on the band size measuring tape adjacent the other end of the band size measuring tape. This is a useful alternative to the second buckle.

In one embodiment of the invention there is provided a measuring device in which the complementary locking members comprise hook and eye fasteners and in which one part of the hook and eye fasteners is mounted on the elasticated portion and the other part of the hook and eye fasteners is mounted on the band size measuring tape adjacent the other end of the band size measuring tape. Velcro (Registered Trade Mark®) is seen as a particularly preferred implementation of hook and eye fastener to use.

In one embodiment of the invention there is provided a measuring device in which the first buckle forms a loose fit around the band size measuring tape so that the band size measuring tape is substantially freely slidable through the first buckle. By forming a loose fit around the band size measuring tape, the tape can slide freely past the first buckle allowing for expansion and contraction of the loop as the wearer inhales and exhales respectively. This will result in a more accurate band size measurement being taken.

In one embodiment of the invention there is provided a measuring device in which there is provided a clasp mounted intermediate the ends of the band size measuring tape to allow opening and closing of the loop formed by the band size measuring tape. By providing a clasp, the breast measuring device can be secured around the wearer's torso just below the breast and released from the wearer quickly with minimum difficulty. The band size measuring tape may first of all be adjusted to the wearer's approximate band size by threading the end of the band size measuring tape through the first buckle and securing the end of the band size measuring tape in that position before the band size measuring tape is looped around the wearer's torso and secured in a looped configuration with the clasp. Thereafter, the band size measuring tape can be finely adjusted to the exact band size of the wearer. It is envisaged that this technique will be easier than the wearer having to thread the end of the band size measuring tape through one or two buckles while the band size measuring tape is surrounding their torso and as a result the band size measuring tape is less likely to have twists in it which could have led to an inaccurate band size reading.

In one embodiment of the invention there is provided a measuring device in which there are a pair of cup size measuring tapes mounted on and extending substantially perpendicular to the band size measuring tape.

In one embodiment of the invention there is provided a measuring device in which the cup size measuring tape is slidably mounted on the band size measuring tape and is free to move along the band size measuring tape. By providing a slidable cup size measuring tape, the cup size measuring tape can be positioned accurately leading to less likelihood of errors in measurement occurring.

In one embodiment of the invention there is provided a measuring device as claimed in any preceding claim in which the cup size measuring tape is constructed from a predominantly transparent tape. A transparent tape will allow the centre of the nipple to be seen through the tape leading to less errors of measurement. Furthermore, this will make the device easier to use.

In one embodiment of the invention there is provided a measuring device in which the buckle is constructed from a predominantly transparent material. By having the buckle constructed from a transparent material, it will be possible to see the point along the tape in the buckle that the end of the band size measuring tape overlaps with the remainder of the tape thereby providing the band measurement. Again, this will simplify reading the measurement and will result in a device that is easier to use.

In one embodiment of the invention there is provided a measuring device in which there are provided a plurality of band size zones marked out on the band size measuring tape and in which there is provided a band size buffer zone intermediate each adjacent pair of band size zones.

In one embodiment of the invention there is provided a measuring device in which there are provided a plurality of cup size zones marked out on the cup size measuring tape and in which there is provided a cup size buffer zone intermediate one or more adjacent pairs of cup size zones.

BRIEF DESCRIPTION OF THE DRAWINGS

The invention will now be more clearly understood from the following description of some embodiments thereof given by way of example only with reference to the accompanying drawings, in which: —

DETAILED DESCRIPTION OF THE DRAWINGS

Figure 1:
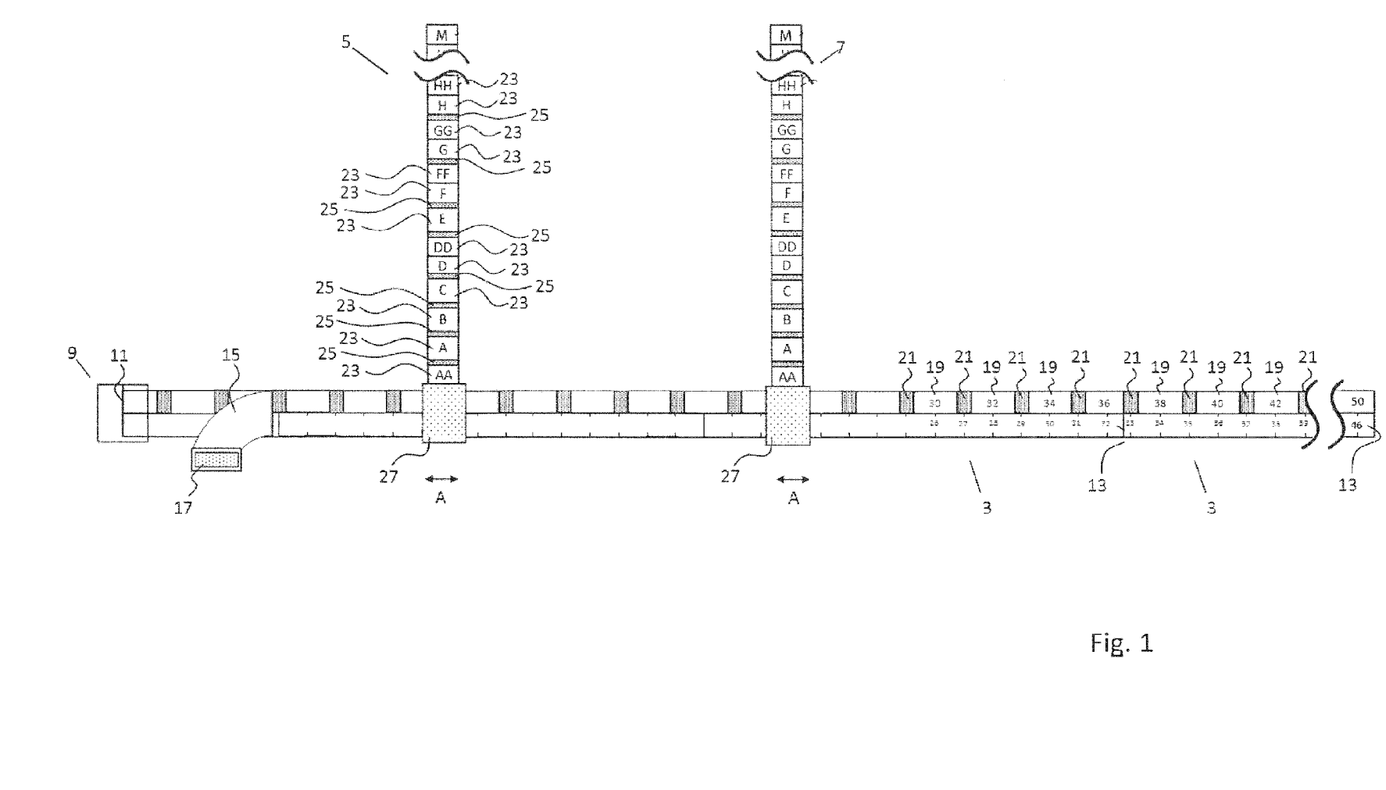
FIG. 1 is a front view of a measuring device for determining bra size according to the invention.

Referring to FIG. 1, there is shown a front view of a measuring device for determining bra size, indicated generally by the reference numeral 1, comprising a band size measurement tape 3 and a pair of cup size measurement tapes 5, 7 mounted on the band size measurement tape and extending substantially perpendicular thereto. The cup size measurement tapes 5, 7 are slidably mounted on the band size measurement tape and are slidable along the length of the band size measurement tape as indicated by arrows A. The measuring device 1 further comprises a buckle 9 mounted on one end 11 of the band size measuring tape 3 through which the other free end 13 of the band size measuring tape 3 may be led thereby forming a loop with the band size measuring tape 3 to surround the torso (not shown) of a person being measured.

The measuring device additionally comprises means to releasably secure the band size measuring tape in the looped configuration. In this instance, the means to releasably secure the band size measuring tape in a looped configuration comprises a strip of elasticated material 15 connected at one of its ends to the band size measuring tape and having one part 17 of a complementary hook and eye fastener arrangement mounted at its other end. The means to releasably secure the band size measuring tape in the looped configuration further comprises the other part of the complementary hook and fastener arrangement (not shown) which is mounted on the rear side of portion of the band size measuring tape. The means to releasably secure the band size measuring tape in a looped configuration and its operation will be elaborated upon and illustrated in more detail with reference to FIGS. 2(a) to 2(c) inclusive below.

Referring still to FIG. 1, the band size measuring tape 3 comprises a flexible tape with indicia printed on one face thereof. The indicia comprises a plurality of band size zones 19 marked out on the band size measuring tape and there is provided a band size buffer zone 21 intermediate each adjacent pair of band size zones 19. In the embodiment shown, the band size measuring tape is divided into an upper portion and a lower portion. The upper portion has the plurality of band size zones 19 and band size buffer zones 21 printed thereon, and the lower portion has additional indicia printed thereon, in this case the markings of a standard measuring tape. If a measurement falls within the band size buffer zone, this indicates that the person being measured is between sizes, specifically between the two sizes separated by the buffer zone.

Instead of having an upper and a lower portion, the entire tape could be taken up by the band size zones 19 and the band size buffer zones 21. Alternatively, the lower portion or indeed a third portion (not shown) could be provided with band size zones calculated according to another manufacturer's guidelines.

For reasons of clarity, and to aid the readers understanding of the invention, a brief description will now be provided on the various measurement methodologies and systems used in some of the different regions throughout the World and how the markings on the measuring device according to the invention are determined. In the UK for example, bras are currently manufactured/supplied in only even band sizes (32, 34, 36, 38 and so on). This band size is based on actual inch values with 4 or 5 inches added to the actual inch value. As the end band size must be even (to correspond with what is available to the consumer), 4 is added to all even actual inch values and 5 is added to all uneven actual inch values to ensure the end result is always an even band size. Therefore, an actual measurement of 29" in the UK will equate to a 34 band (29"+5=band 34) and an actual measurement of 30" will also equate to a 34 band (30"+4=band 34).

In regions using metric units (cm), the increments are 5 cm (roughly equivalent to 2 inches). Although the principle of band values is similar in all regions, the starting value scale for almost every region band size is different and because of this, each region has their own different calculation method to arrive at an given band/cup size. These calculations are quite confusing and can often require the need for a reference chart that is open to interpretation and error by the user. The breast measuring device described in this specification is designed to carry out these calculations for any given region and require no external reference. It is intended that the tape will be individually designed for any of the following regions or a combination thereof (as a manufacturer may choose to put measurements for more than one region on a single breast measuring device): The United States; the United Kingdom; Europe (parts thereof) & Japan; Australia & New Zealand; Belgium, Spain & France; Italy & Czech Republic. The table below shows a small sample of the differences between the bra sizes in some of the different regions. The table below is in accordance with the current standards at the time of the earliest priority date of the specification.

| US (Based on inch) | UK (Based on inch) | France/Spain/Belgium (Based on cm) | Australia/NZ (Based on Inch) | Europe/Japan (Based on cm) |
|---|---|---|---|---|
| 32AA | 32AA | 85AA | 10AA | 70AA |
| 32A | 32A | 85A | 10A | 70A |
| 32B | 32B | 85B | 10B | 70B |
| 32C | 32C | 85C | 10C | 70C |
| 32D | 32D | 85D | 10D | 70D |
| 34AA | 34AA | 90AA | 12AA | 75AA |
| 34A | 34A | 90A | 12A | 75A |
| 34B | 34B | 90B | 12B | 75B |
| 34C | 34C | 90C | 12C | 75C |
| 34D | 34D | 90D | 12D | 75D |

The cup size measuring tapes 5, 7 each comprise a substantially transparent piece of flexible tape with indicia printed on one side thereof. There are provided a plurality of cup size zones 23 marked out on the cup size measuring tapes 5, 7 and there are provided a plurality of cup size buffer zones 25 intermediate one or more adjacent pairs of cup size zones. Each of the cup size measuring tapes 5, 7 is connected to the band size measuring tape 3 by way of a loop 27 at the end of the cup size measuring tape 5, 7 which surrounds the band size measuring tape 3. The buckle 9 is constructed from a transparent material.

Figure 2A:
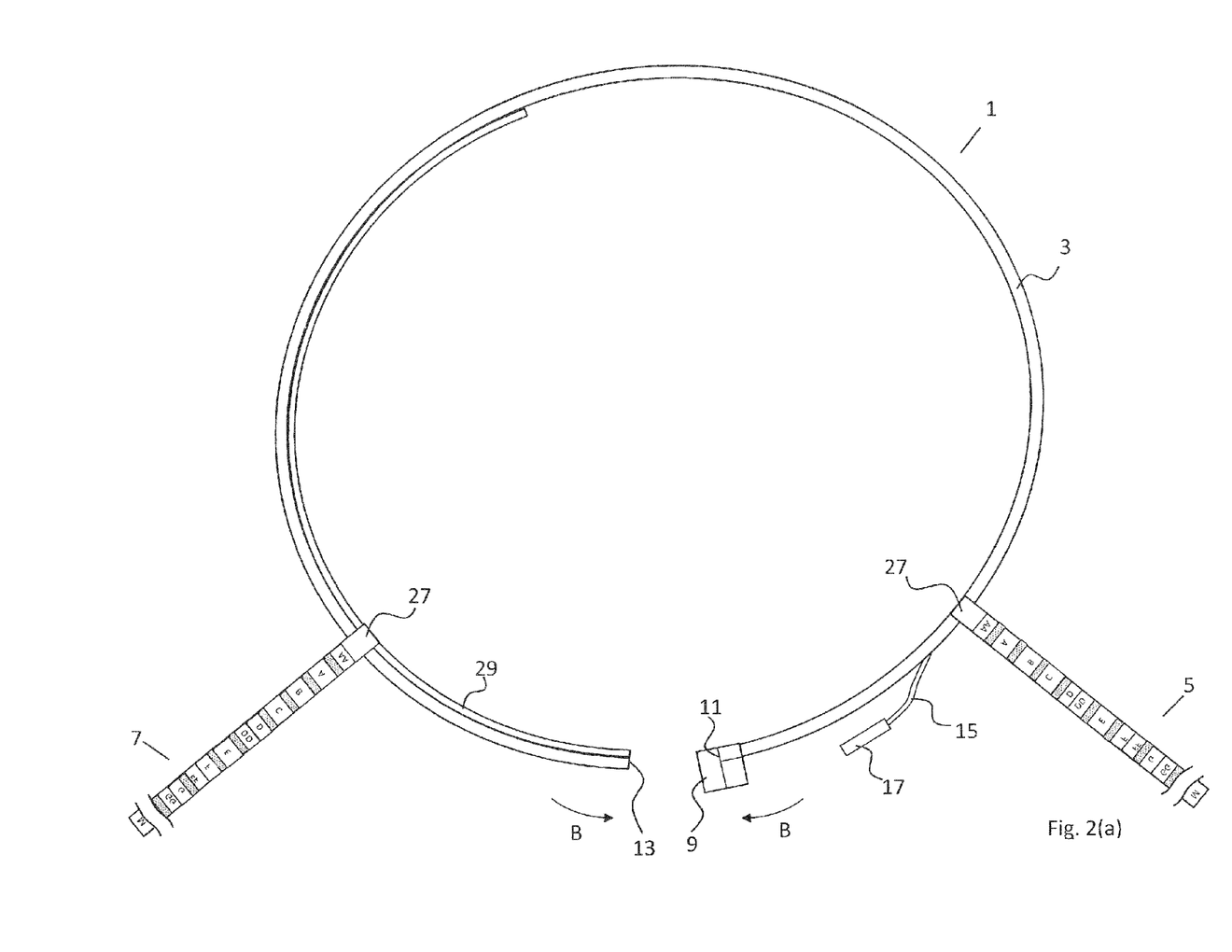
FIGS. 2(a) to 2(c) are top plan views of the measuring device shown in FIG. 1 illustrating the band size measurement tape being secured in a loop.
Figure 2B:
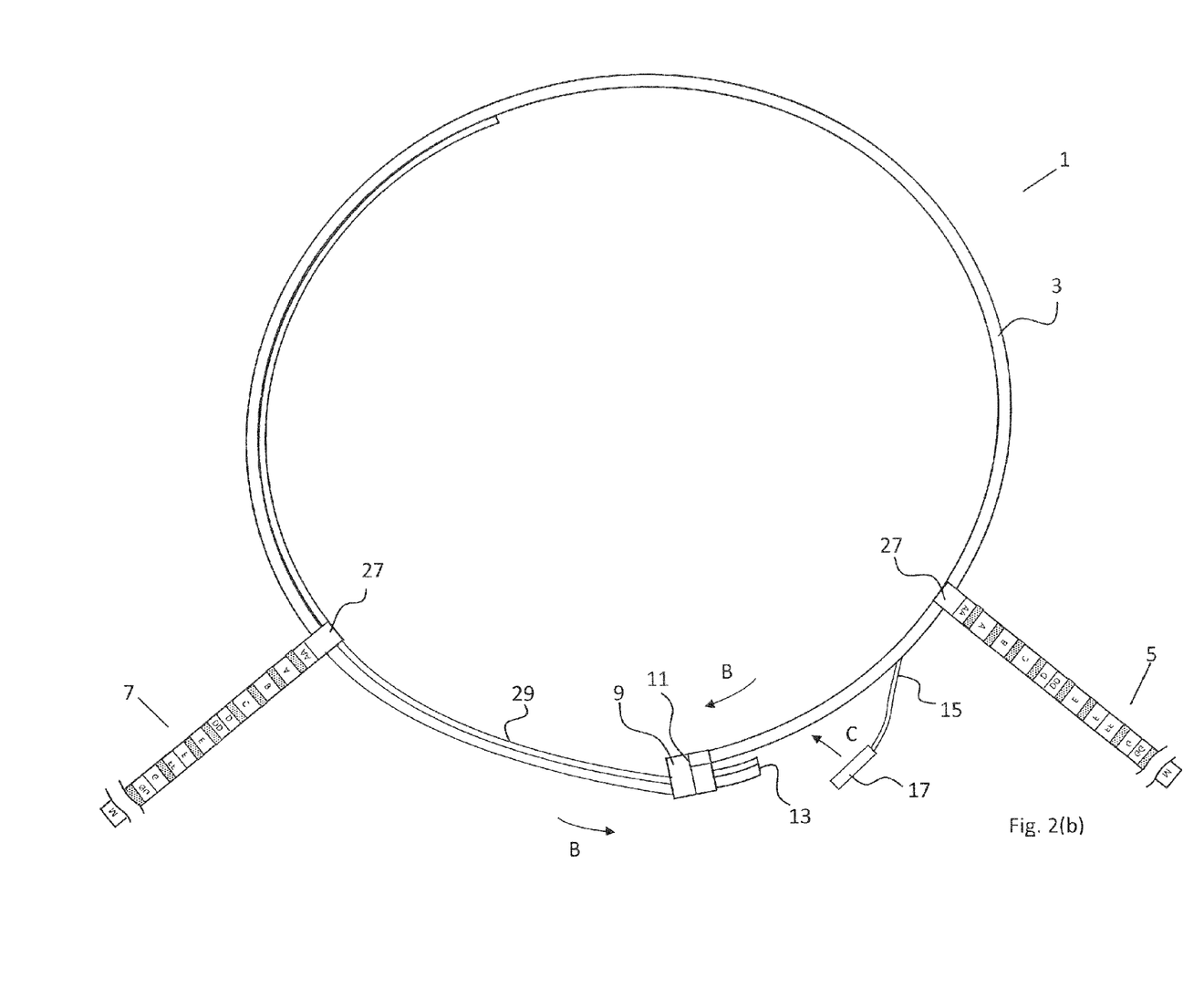
Figure 2C:
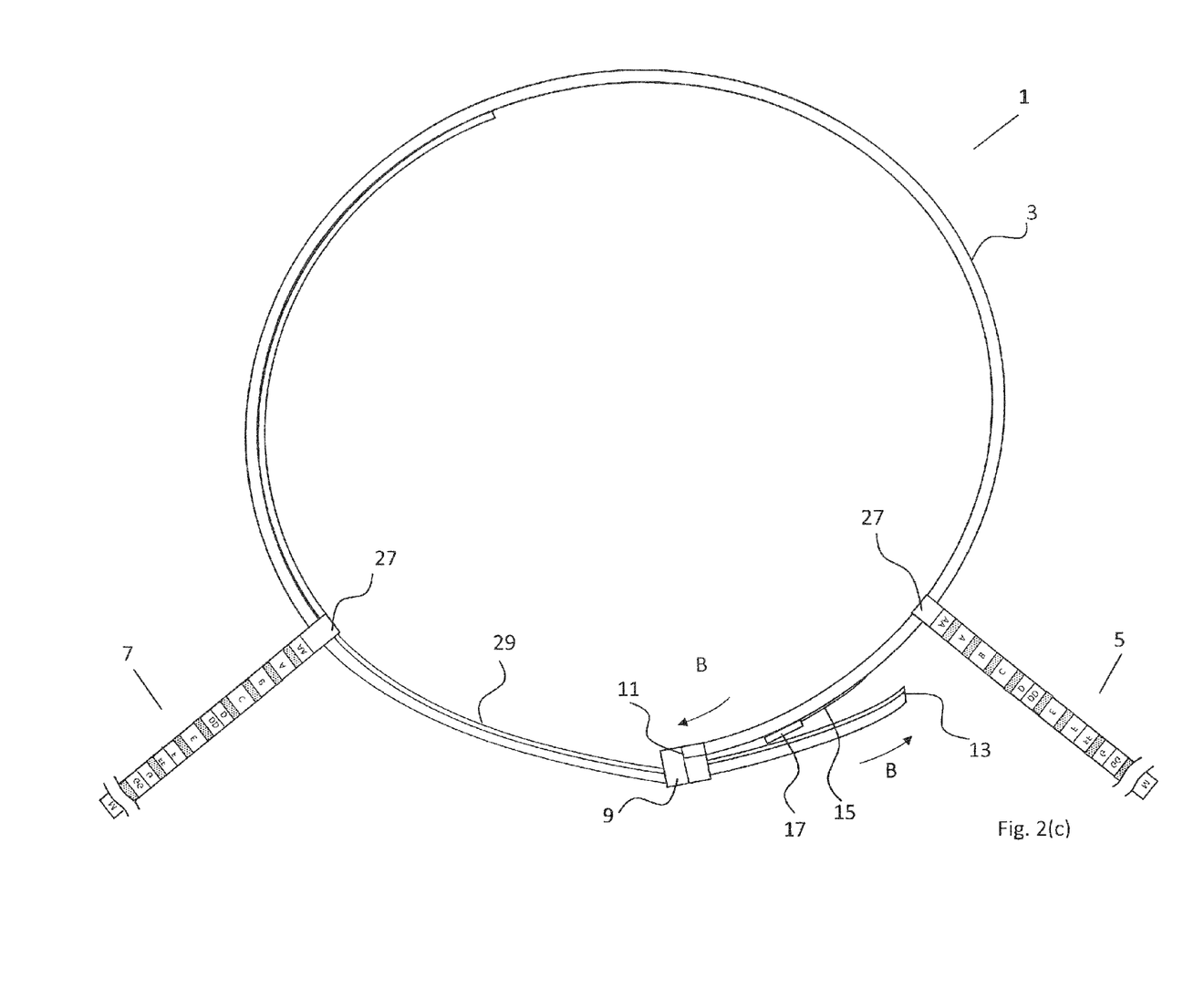

Referring to FIGS. 2(a)-2(c) inclusive, there is shown a plurality of top plan views of the measuring device according to the present invention. The other part of the complementary hook and eye fastener arrangement 29 is shown mounted on the rear side of portion of the band size measuring tape. FIGS. 2(a) to 2(c) show in sequence the steps taken to form a loop and secure the band size measurement tape in a looped configuration. In FIG. 2(a), the measurement device is led around the woman's torso just below the breasts and the ends 11, 13 are brought towards each other, as indicated by the arrows B. In FIG. 2(b), the end 13 is introduced into the buckle 9. The one part 17 of the hook and eye fastener system is laid up against the band size measurement tape 3 and the end 13 of the band size measurement tape is pulled through the buckle 9 until the loop of the band size measurement tape forms a snug fit around the woman's torso. Once the loop of the band size measurement tape forms a snug fit around the woman's torso, the other part 29 of the hook and eye fastener system is brought into engagement with the first part 17 of the hook and eye fastener system, as shown in FIG. 2(c), thereby securing the loop in position.

Due to the fact that the first part 17 of the hook and eye fastener system is mounted on an elasticated portion 15, the woman can breathe in and out normally and the elasticated portion will allow the circumference of the loop to increase and decrease by a limited amount corresponding to the expansion of the woman's torso as she inhales and exhales. The correct measurement of the band size should be taken when the woman has exhaled rather than inhaled so the configuration ensures that the measurement taken is not erroneous due to having been taken at a time of inhalation. Once the loop is secured in place after the woman has exhaled, the loop can expand by a limited amount to allow the woman to breathe in but will return to the original, secured position. The band measurement can be read off the band by looking through the buckle 9 at the point where the band size measurement tape passes over the end 9 of the band size measurement tape. A line or other marking may be provided on the buckle 9 to clearly indicate the position of the end 9 of the band size measurement tape, as the end will be obscured from view by the other overlapping part of the band size measurement tape.

Importantly, the elastic portion is provided and connected to the band size measuring tape at a point after the band size measuring tape has passed through the buckle. This will ensure that the torso measurement is not skewed by the elasticated portion being stretched leading to a false reading of the band size.

Figure 3:
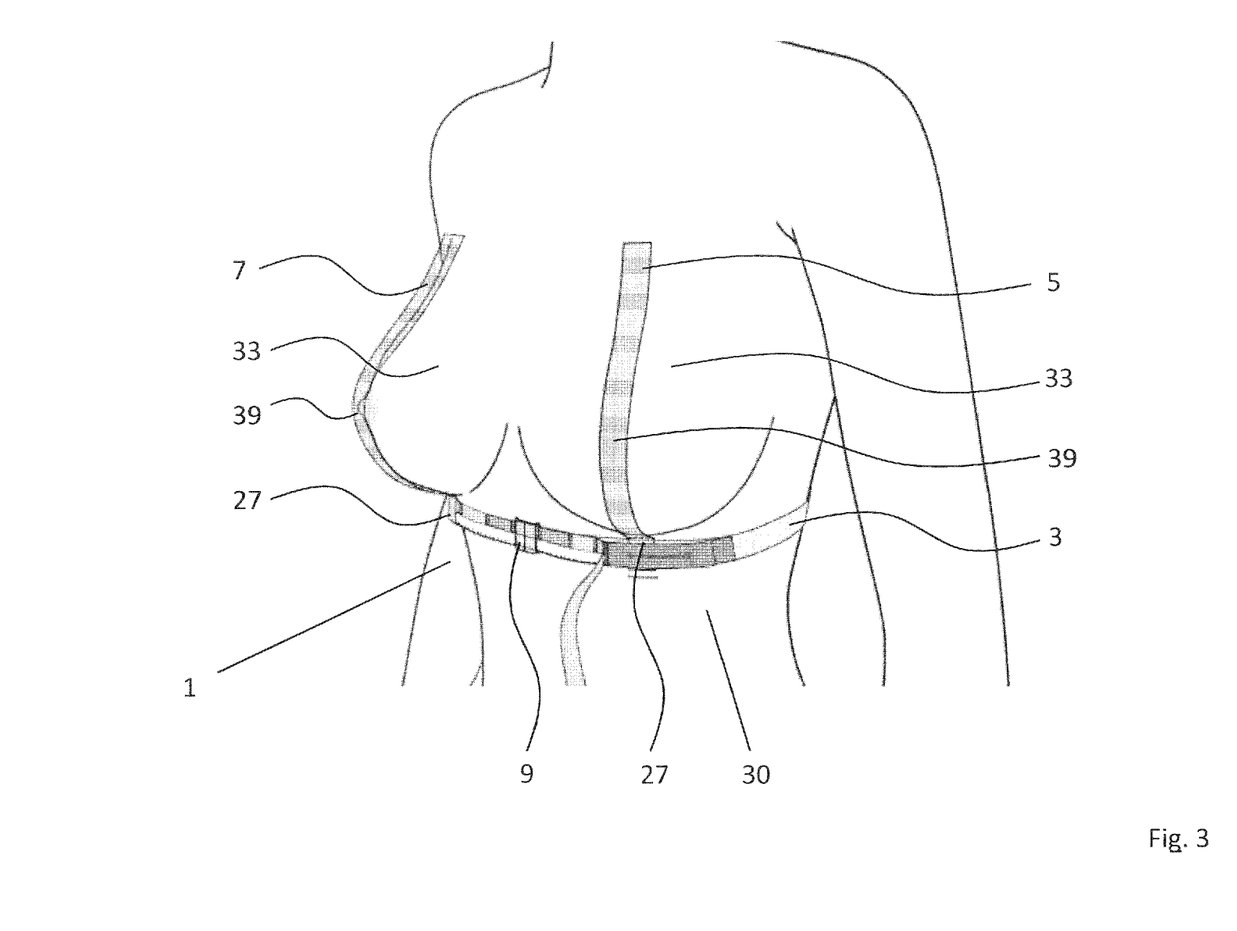
FIG. 3 is a front view of a woman's torso with the measuring device according to the invention in position.

Referring to FIG. 3, there is shown a front view of a woman's torso 30, with the measuring device according to the invention, indicated generally by the reference numeral 1, looped around the torso 30 in a position just below the breasts 33 to measure the appropriate bra size. It is envisaged that various different types of buckle could be provided without departing from the spirit of the invention. The buckle 9 is a simple loop that allows the band size measuring tape 3 to pass therethrough and to form the looped configuration. Furthermore, the buckle 9 is transparent so that the point at which the end 11 of the band size measuring tape intersects or crosses over the remainder of the band size measuring tape is clearly visible through the buckle 35.

More importantly though, FIG. 3 illustrates the operation of the cup size measuring tapes 5, 7. Once the band size measuring tape has been secured in a looped configuration around the torso 30, the cup size measuring tapes 5, 7 are slid along the band size measuring tape 3 to a point where they are substantially central relative to the nearest breast 33, in line with the position of the nipple. Once in a position below and substantially central relative to the nearest breast, the cup size measuring tape is drawn upwards over the surface of the breast and over the nipple 39. The cup size is determined by seeing which cup size zone of the substantially transparent cup size measurement tape the nipple 39 is visible through. It is quite likely that the left and right breast 33 sizes may differ in which case the cup size zone that denotes the larger cup size may be selected for the bra. This is a core concept of the present invention, namely that the cup size is measured from below the breast up to the nipple.

Figure 4:
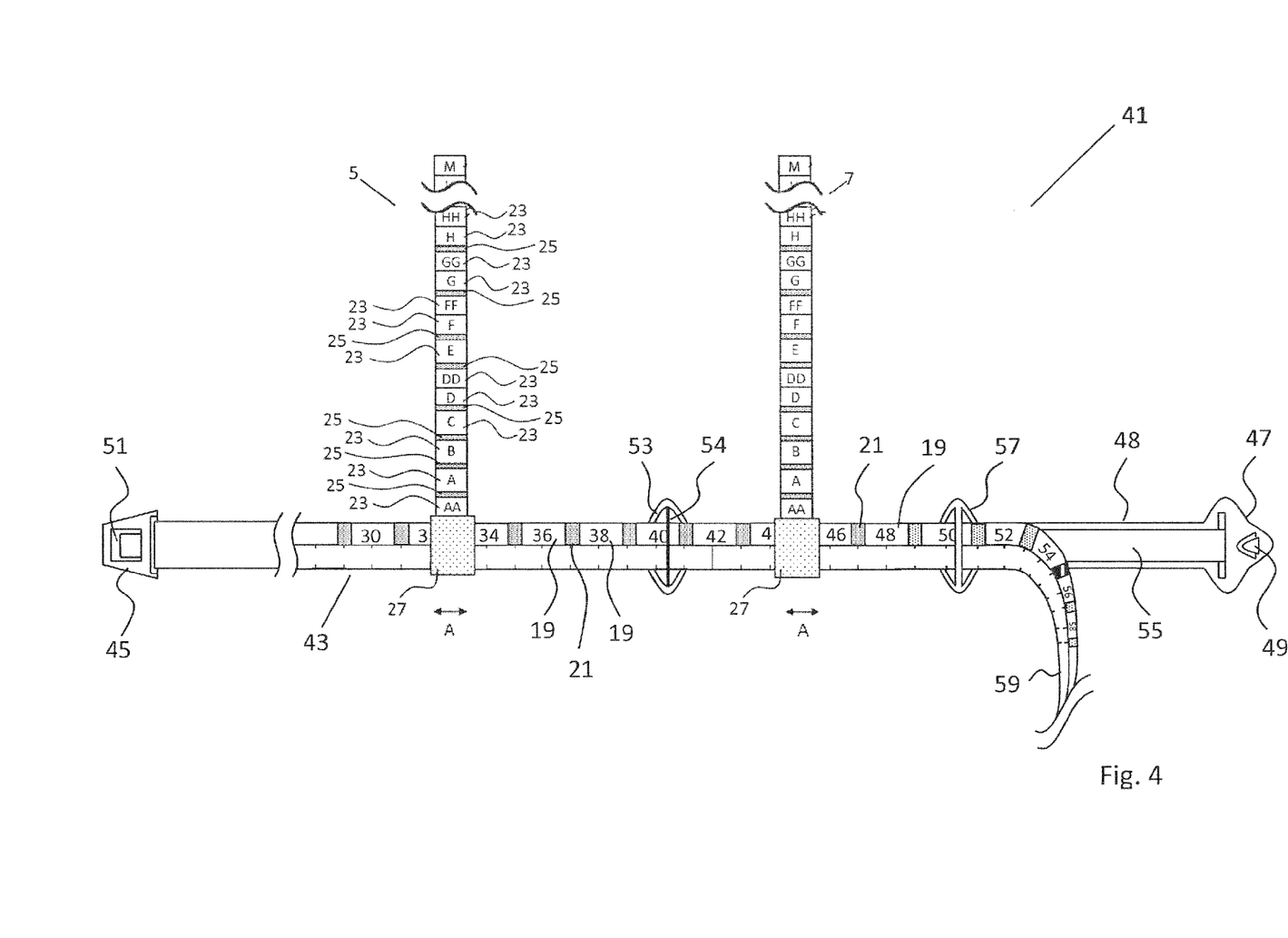
FIG. 4 is a front view of an alternative embodiment of measuring device for determining bra size according to the invention.
Figure 5A:
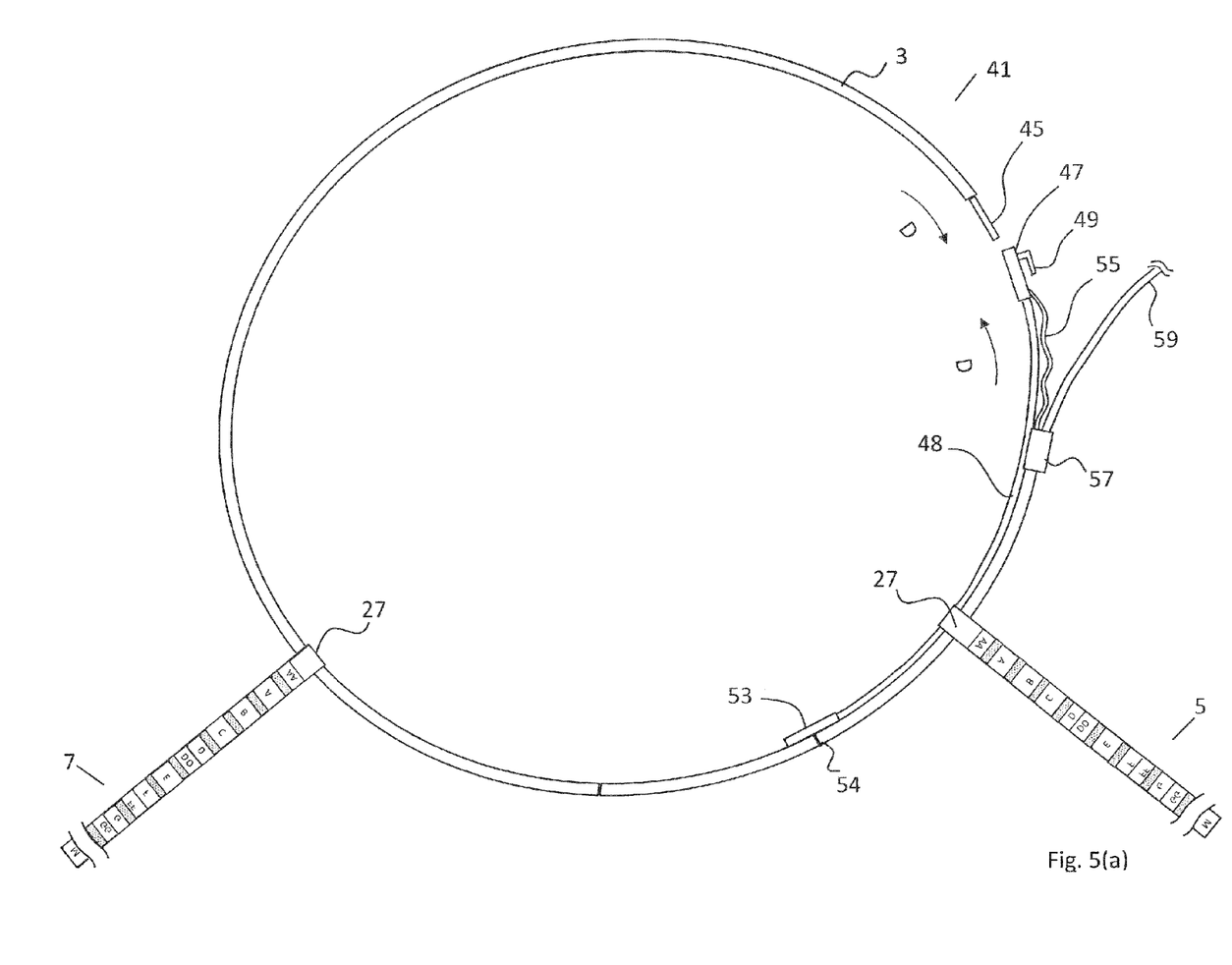
FIGS. 5(a) to 5(c) are top plan views of the measuring device shown in FIG. 4 illustrating the band size measurement tape being secured in a loop.
Figure 5B:
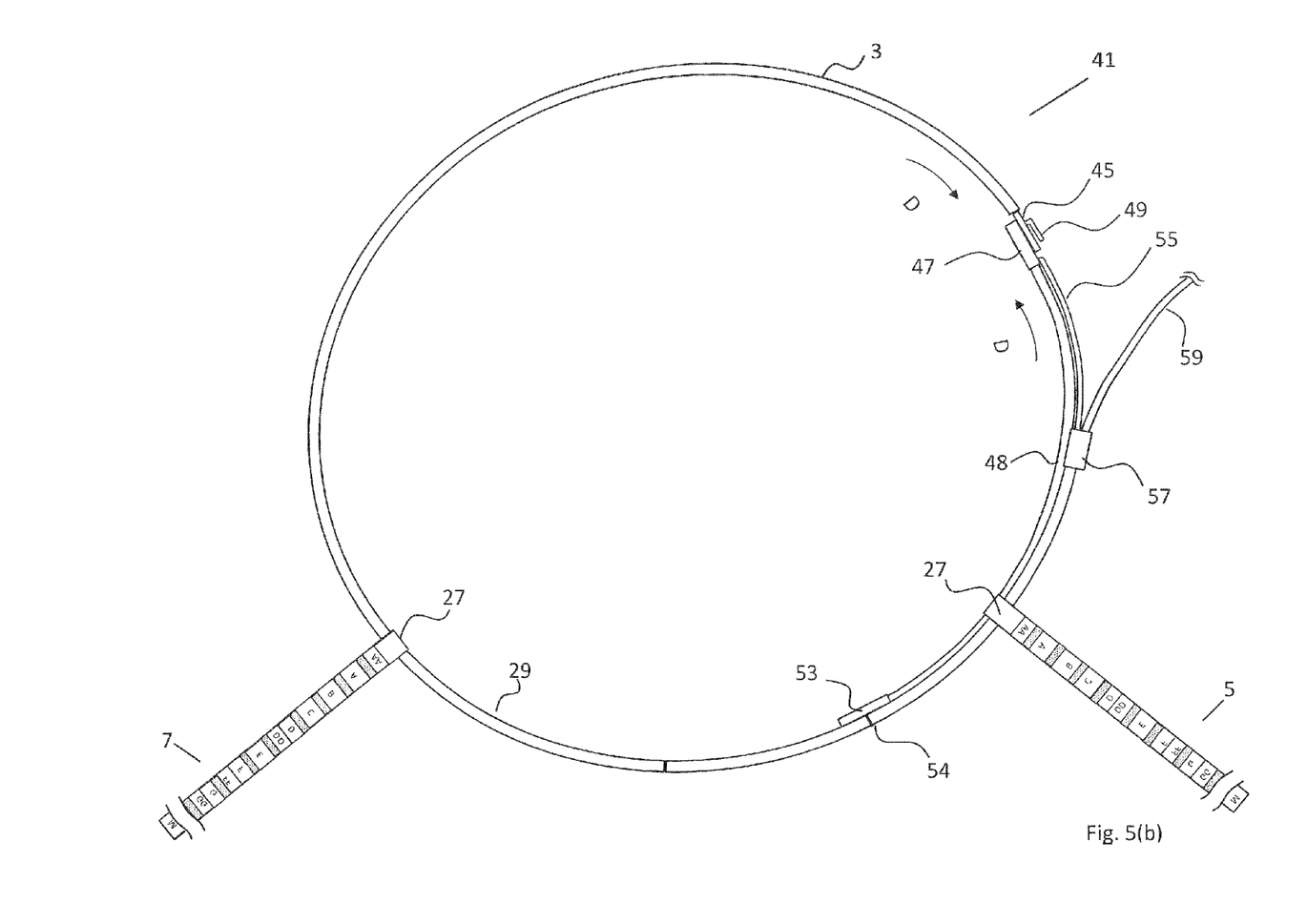
Figure 5C:
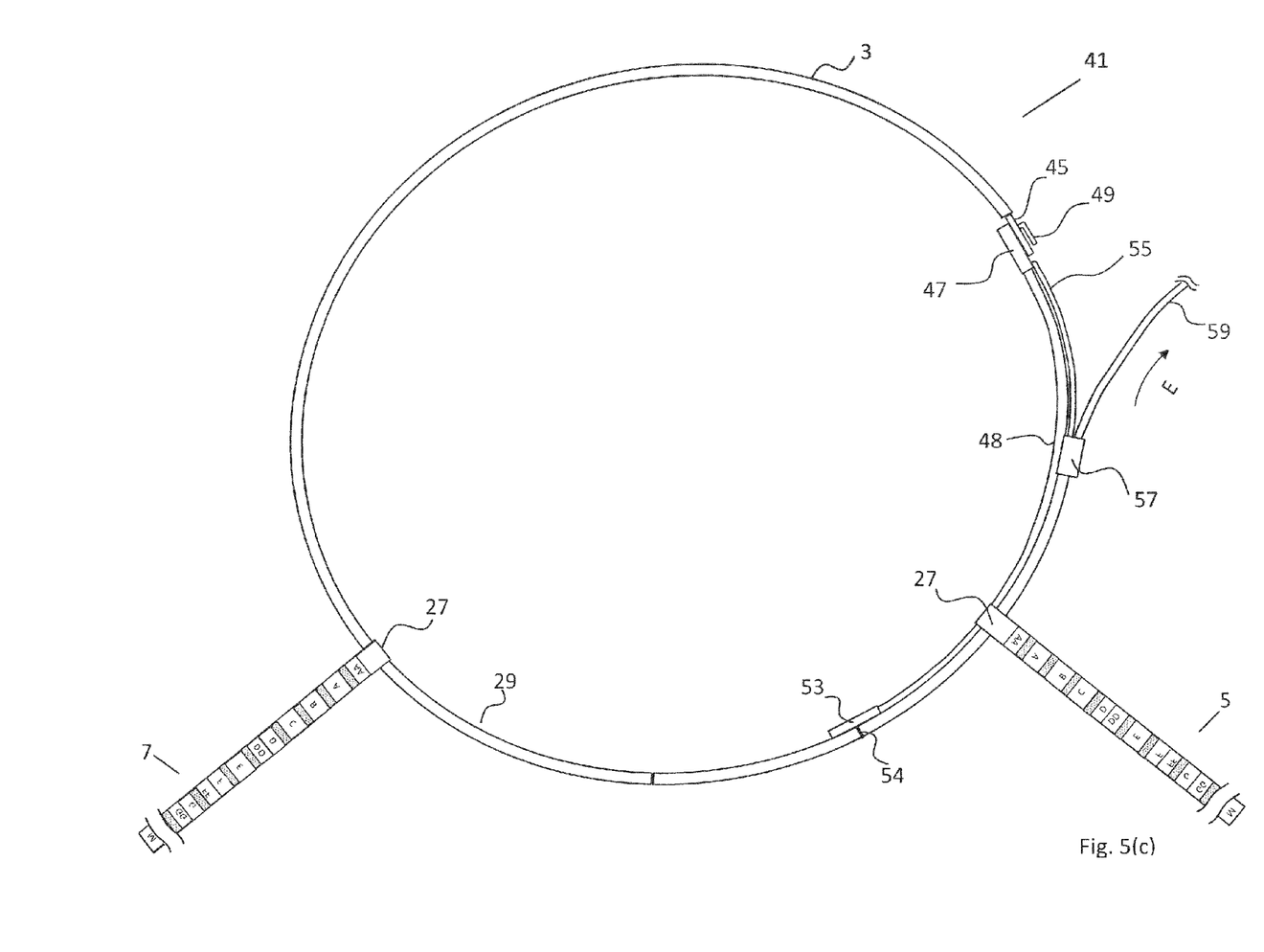

Referring to FIGS. 4 and 5, there are shown various views of an alternative embodiment of breast measuring device for determining bra size according to the present invention, indicated generally by the reference numeral 41 and where like parts have been given the same reference numerals as before. Referring specifically to FIG. 4, there is shown a band size measuring tape 43 having indicia printed thereon indicative of band sizes 19 separated by band size buffer zones 21. The band size measuring tape 43 has a clasp, in this case a two part clasp, one part of which 45 is located at one end of the band size measuring tape and the other part of which 47 is located at one end of a band size measuring tape insert 48. The band size measuring tape insert 48 is considered an extension of and therefore a part of the band size measuring tape 43. The part 47 of the clasp comprises a hook 49 and the part 45 of the clasp comprises a throughbore 51 for reception of the hook 49.

There is provided a first buckle 53 slidably mounted on the end of the band size measuring tape insert 48 opposite the end with the clasp portion 47 thereon. The first buckle 53 fits loosely around the band size measuring tape 43 so that it is easily slidable along the band size measuring tape. The buckle 53 has an indicator bar 54 located in front of the band size measuring tape 43. There is further provided an elasticated portion 55 connected at one end to the clasp part 47 and connected at its other end to a second buckle 57. The second buckle fits snugly around the band size measuring tape 43 so that with appropriate force, the band size measuring tape may move through the second buckle 57 however there is sufficient frictional force to keep it in position along the band size measuring tape 43 in the absence of a moving force being applied to it by a user of the breast measuring device. The cup size measuring tapes 5, 7 are identical to the ones shown in FIGS. 1 to 3 inclusive and are slidable along the band size measuring tape 43.

Referring now to FIGS. 5(a) to 5(c) inclusive, the operation of the second embodiment of breast measuring device will be described in greater detail. Referring first of all to FIG. 5(a), the end 59 of the band size measuring tape 43 is pulled through the second buckle 57 to a point where the first buckle 53 is located along the band size measuring tape 43 with the indicator bar 54 over a band size zone 19 estimated to be at or preferably slightly larger than the actual band size of the woman being measured. The frictional force of the band size measuring tape 43 in the second buckle 57 will hold the band size measuring tape in this position. Referring now to FIG. 5(b), the band size measuring tape 43 is then drawn around the torso of the woman being measured (who may of course be measuring themselves) just below the height of their breasts and the end of the band size measuring tape 43 with the clasp part 45 thereon and the clasp part 47 mounted on the band size measuring tape insert 48 are drawn together in the direction of the arrows D. The clasp part 47, and more specifically the hook 49 of the clasp part 47, is used to engage the clasp part 45, and more specifically the throughbore 51 of the clasp part 45, to form a loop in the band size measuring device formed by the band size measuring tape 43 and the band size measuring tape insert 48. Once the loop has been formed (as illustrated in FIG. 5(b)), the band size measuring tape is adjusted to the correct band size by pulling the end 59 of the band size measuring tape 43 through the second buckle 57 in the direction of arrow E in FIG. 5(c). The indicator bar 54 will be located along the band size measuring tape over one of the band size zones 19 or over one of the band size buffer zones 21 and from this the user of the breast measurement device can determine the actual band size of the wearer of the device. The cup size of each breast is measured using the cup size measuring tapes 5, 7 and the appropriate cup size is chosen in the manner described previously.

It will be understood that in this configuration shown in FIG. 5(*c*), due to the fact that the first buckle 53 is easily slidable along the band size measuring tape 43 and the second buckle 57 catches the band size measuring tape 43, the elasticated portion 55 becomes an integral part of the loop in the band size measuring tape. In this way, the elasticated portion allows temporary expansion and contraction of the loop formed in the band size measuring tape as the wearer inhales and exhales.

In the embodiment shown in FIGS. 4 and 5(*a*) to 5(*c*), in order to ensure correct alignment of the first buckle 53 and the indicator bar 54 with the band size measuring tape, the band size measuring tape insert 48 is preferably constructed from a flexible yet semi-rigid material, such as a plastics material. This will allow bending of the band size measuring tape insert 48 around the curvature of the body but at the same time will hold the first buckle 53 mounted at one end of the band size measuring tape insert 48 spaced apart from the clasp part 47 mounted at the other end of the band size measuring tape insert.

It can be seen from the foregoing description of the embodiments and with reference to FIG. 3 in particular that both the band size measurement and the cup size measurement will be visible at the same time. There will be no need for reference to lookup tables, mental arithmetic or for the woman to memorize the measurements. Instead, the bra size will be immediately visible and apparent by reading the band size measuring tape and the cup size measuring tape. Furthermore, it will be apparent that the assistance of a third party will not be necessary and rather the measuring device can be used effectively in the comfort of the woman's home, if desired, or in a fitting room.

It will be understood that various modifications could be made to the embodiments hereinbefore described without departing from the spirit of the invention. For example, it is envisaged that the cup size buffer zone and/or the band size buffer zones could be removed with the band size zones and or the cup size zones abutting against each other. Furthermore, in the embodiments shown a hook and eye arrangement or a buckle 9 has been used as the means for securing the band size measurement tape in a looped configuration around the torso however other arrangements would be apparent to the person skilled in the art. In the embodiment shown, a pair of cup size measuring tapes is provided however one would be sufficient if used in turn to measure both breasts 33. Furthermore, the cup size measuring tapes are substantially transparent however this is advantageous but not essential. In addition to the above, the cup size measuring tape could be detachably mounted to the band size measuring tape.

It is envisaged that the measuring tape according to the present invention, and in particular the band size measuring tape could be a useful tape to take accurate measurements of other parts of the human or animal anatomy. The use of the elasticated portion following the buckle that allows for limited expansion and contraction and more consistently accurate measurements to be taken is quite advantageous for other parts of the anatomy, not simply for breast and bra measurement. Indeed, the band size measuring tape portion, when used on its own, could be used simply for accurate torso measurement, for bicep/tricep measurement, thigh muscle measurement and stomach circumference measurement to name but a few.

Furthermore, it is envisaged that graphics such as pictorial and/or written instructions may be provided on a side of the band size measuring tape, for example, the reverse side of the tape to instruct the user on the use of the tape.

In this specification the terms "comprise, comprises, comprised and comprising" and the terms "include, includes, included and including" are all deemed totally interchangeable and should be afforded the widest possible interpretation.

The invention is in no way limited to the embodiment hereinbefore described but may be varied in both construction and detail within the scope of the claims.

The invention claimed is:

1. A breast measuring device for determining bra size comprising a band size measuring tape and a cup size measuring tape mounted on and extending substantially perpendicular to the band size measuring tape, the band size measuring tape comprising a flexible tape having indicia printed on one side thereof indicative of a plurality of band sizes, the cup size measuring tape comprising a flexible tape capable of following the contour of a breast and having indicia printed on one side thereof indicative of a plurality of cup sizes, and in which there is provided a first buckle mounted on a first end of the band size measuring tape through which a second end of the band size measuring tape may be led thereby forming a loop with the band size measuring tape to surround the torso of a person being measured and means to releasably secure the band size measuring tape in the looped configuration and in which there is provided an elasticated portion to permit limited expansion and contraction of the circumference of the loop in the band size measuring tape when secured in a looped configuration.

2. The breast measuring device as claimed in claim 1 in which the elasticated portion has attached thereto the means to releasably secure the band size measuring tape in the looped configuration.

3. The breast measuring device as claimed in claim 2 in which the elasticated portion is mounted on the band size measuring tape intermediate the first and second ends of the band size measuring tape and adjacent to one of the first and second ends thereof.

4. The breast measuring device as claimed in claim 2 in which the means to releasably secure the band size measuring tape in the looped configuration comprises a second buckle mounted on the elasticated portion and through which the end of the band size measuring tape led through the first buckle may also be led and secured in position.

5. The breast measuring device as claimed in claim 2 in which the means to releasably secure the band size measuring tape in the looped configuration comprises a pair of complementary locking members and in which the elasticated portion has one part of the pair of complementary locking members mounted thereon for engagement of the other part of the pair of complementary locking members which in turn is mounted on the band size measuring tape adjacent the other end of the band size measuring tape.

6. The breast measurement device as claimed in claim 5 in which the complementary locking members comprise hook and eye fasteners and in which one part of the hook and eye fasteners is mounted on the elasticated portion and the other part of the hook and eye fasteners is mounted on the band size measuring tape adjacent the other end of the band size measuring tape.

7. The breast measuring device as claimed in claim 1 in which the first buckle forms a loose fit around the band size measuring tape so that the band size measuring tape is substantially freely slidable through the first buckle.

8. The breast measuring device as claimed in claim 1 in which there is provided a clasp mounted intermediate the first and second ends of the band size measuring tape to allow opening and closing of the loop formed by the band size measuring tape.

9. The breast measuring device as claimed in claim 1 in which there are a pair of cup size measuring tapes mounted on and extending substantially perpendicular to the band size measuring tape.

10. The breast measuring device as claimed in claim 1 in which the cup size measuring tape is slidably mounted on the band size measuring tape and is free to move along the band size measuring tape.

11. The breast measuring device as claimed in claim 1 in which the cup size measuring tape is constructed from a predominantly transparent tape.

12. The breast measuring device as claimed in claim 1 in which the first buckle is constructed from a predominantly transparent material.

13. The breast measuring device as claimed in claim 1 in which there are provided a plurality of band size zones marked out on the band size measuring tape and in which there is provided a band size buffer zone intermediate each adjacent pair of band size zones.

14. The breast measuring device as claimed in claim 1 in which there are provided a plurality of cup size zones marked out on the cup size measuring tape and in which there is provided a cup size buffer zone intermediate one or more adjacent pairs of cup size zones.

* * * * *